United States Patent

Nosaka et al.

[11] Patent Number: 6,105,417
[45] Date of Patent: Aug. 22, 2000

[54] GAS SENSOR

[75] Inventors: Toshikazu Nosaka; Yoshiaki Sakurai; Kazuki Natsukawa; Tsutomu Yotsuya, all of Osaka; Shunsaku Kawabata, Hyogo; Katsumi Nishida, Hyogo; Kazuhiro Nishikawa, Hyogo; Kiyohiro Mori, Osaka; Hiromi Kiyama, Osaka; Yoshinori Omori, Osaka, all of Japan

[73] Assignees: Osaka Prefecture, Osaka; Daido Hoxan Inc., Sapporo, both of Japan

[21] Appl. No.: 09/101,106

[22] PCT Filed: Sep. 19, 1997

[86] PCT No.: PCT/JP97/03318

§ 371 Date: Apr. 15, 1999

§ 102(e) Date: Apr. 15, 1999

[87] PCT Pub. No.: WO98/12548

PCT Pub. Date: Mar. 26, 1998

[30] Foreign Application Priority Data

Sep. 20, 1996 [JP] Japan .................................. 8/249412

[51] Int. Cl.[7] ........................... G01N 27/00; G01N 27/12
[52] U.S. Cl. .............................. 73/31.05; 422/88
[58] Field of Search ............................. 73/31.05; 422/88, 422/90

[56] References Cited

U.S. PATENT DOCUMENTS

| 4,769,548 | 9/1988 | Burtscher et al. . | |
| 5,227,038 | 7/1993 | Smalley et al. | 204/173 |
| 5,334,351 | 8/1994 | Heinze et al. | 422/90 |
| 5,350,794 | 9/1994 | Herron et al. . | |
| 5,395,589 | 3/1995 | Nacson | 422/88 |
| 5,493,094 | 2/1996 | Simmons | 219/121.52 |
| 5,547,748 | 8/1996 | Ruoff et al. | 428/323 |
| 5,587,141 | 12/1996 | Ohshima et al. | 423/445 B |
| 5,876,684 | 3/1999 | Withers et al. | 423/445 B |

FOREIGN PATENT DOCUMENTS

| 25494 | 12/1993 | WIPO . |
| 22176 | 9/1994 | WIPO . |

OTHER PUBLICATIONS

JP 07 072108, Patent Abstracts of Japan, vol. 095, No. 006, Jul. 31, 1995.

JP 07 237912, Patent Abstracts of Japan, vol. 096, No. 001, Jan. 31, 1996.

JP 07 257916, Patent Abstracts of Japan, vol. 096, No. 002, Feb. 29, 1996.

*Primary Examiner*—Daniel S. Larkin
*Attorney, Agent, or Firm*—Armstrong, Westerman, Hattori, McLeland & Naughton

[57] ABSTRACT

Gas sensor materials composed of carbon mixture or metal-containing carbon mixture obtained as evaporated matter by arc discharge which occurs by passing an alternating current or a direct current with electric current density of 0.8 to 3.5 $A/mm^2$ on discharge surfaces of carbon electrodes or metal-containing carbon electrodes in an inert gas under a pressure of 0.1 to 600 torr.

2 Claims, 6 Drawing Sheets

GAS SENSOR

TECHNICAL FIELD

The present invention relates to gas sensor materials.

BACKGROUND ARTS

A gas sensor responds to a specific gas contained in other gases such as air and produces an electric signal, a light signal and the like depending on the concentration of the specific gas. Currently, various gas sensors using a detection method wherein chemical properties such as adsorption, reaction, and light emission are often used to identify gas components have been known. As a conversion method into a signal, there is an energy-conversion method, for example using electromotive force, which directly obtains a sensing signal by contacting gases. However, an energy-control method which converts a change in device properties such as material properties, e.g., electrical resistance, transistor properties and the like, into a signal, is mainly used.

As typical materials for gas sensors, oxides having rather difficult reductiveness, such as $SnO_2$ and $ZnO$ types, are available. Among them, most current commercial devices use a porous sintered body of the $SnO_2$ type, which is n type semiconductor. As semiconductor gas sensors which use such an oxide semiconductor, there are surface control types in which interactive reaction with a gas stays on the surface and bulk control types in which the reaction extends to a semiconductor itself. Among them, most are the surface control type like sensors of combustible gases- In such surface control type sensors, a chemical reaction occurs on a semiconductor surface. However, the activity is often not enough with a pure semiconductor. Therefore, the sensing function is improved by dispersing powder of a noble metal, a metal oxide and the like on the semiconductor particles.

However, to detect a gas by using these conventional gas sensors, it is required to heat the gas up to a temperature on the order of 200° C. to 300° C. Moreover, with those sensors there is insufficient selectivity of gas species because of difficulty in specifying gas species since these conventional gas sensors may respond to many species of gases. Therefore, further improvement is desired.

The main object of the present invention is to provide sensor materials which are able to sense gases at room temperature, and which also are superior in selectivity of the gases sensed.

DISCLOSURE OF THE INVENTION

As a result of a series of research efforts related to the above object, the inventors found that a carbon mixture containing fullerenes obtained by a carbon electrode arc method shows peculiar properties of adsorbing a polar gas and not adsorbing a nonpolar gas at room temperature, has larger surface area and electric conductivity so as to be electrically measured because it is composed of carbon grains. Based on these findings, the inventors evaluated the usefulness of the carbon mixture as a gas sensor material and found that the mixture can sense a gas at a room temperature and is superior in gas selectivity. Further, such a carbon mixture that contains metal obtained by arc discharge, wherein a carbon electrode arranged so as to contain a metal component is used, is improved in sensing ability of gases and has good selectivity, resulting in the present invention.

Namely, the present invention relates to providing the following gas sensor materials:

(1) gas sensor materials composed of carbon mixture obtained as evaporated matter by arc discharge which occurs by passing an alternating current or a direct current with electric current density 0.8 to 3.5 $A/mm^2$ on discharge surfaces of carbon electrodes in an inert gas under a pressure of 0.1 to 600 torr.

(2) gas sensor materials composed of metal-containing carbon mixture obtained as evaporated matter by arc discharge which occurs by passing an alternating current or a direct current with electric current density of 0.8 to 3.5 $A/mm^2$ on discharge surfaces of carbon electrodes containing metal at 0.01 to 30% by weight in an inert gas under a pressure of 0.1 to 600 torr.

BEST MODE FOR CARRYING OUT THE INVENTION

Figure 1:
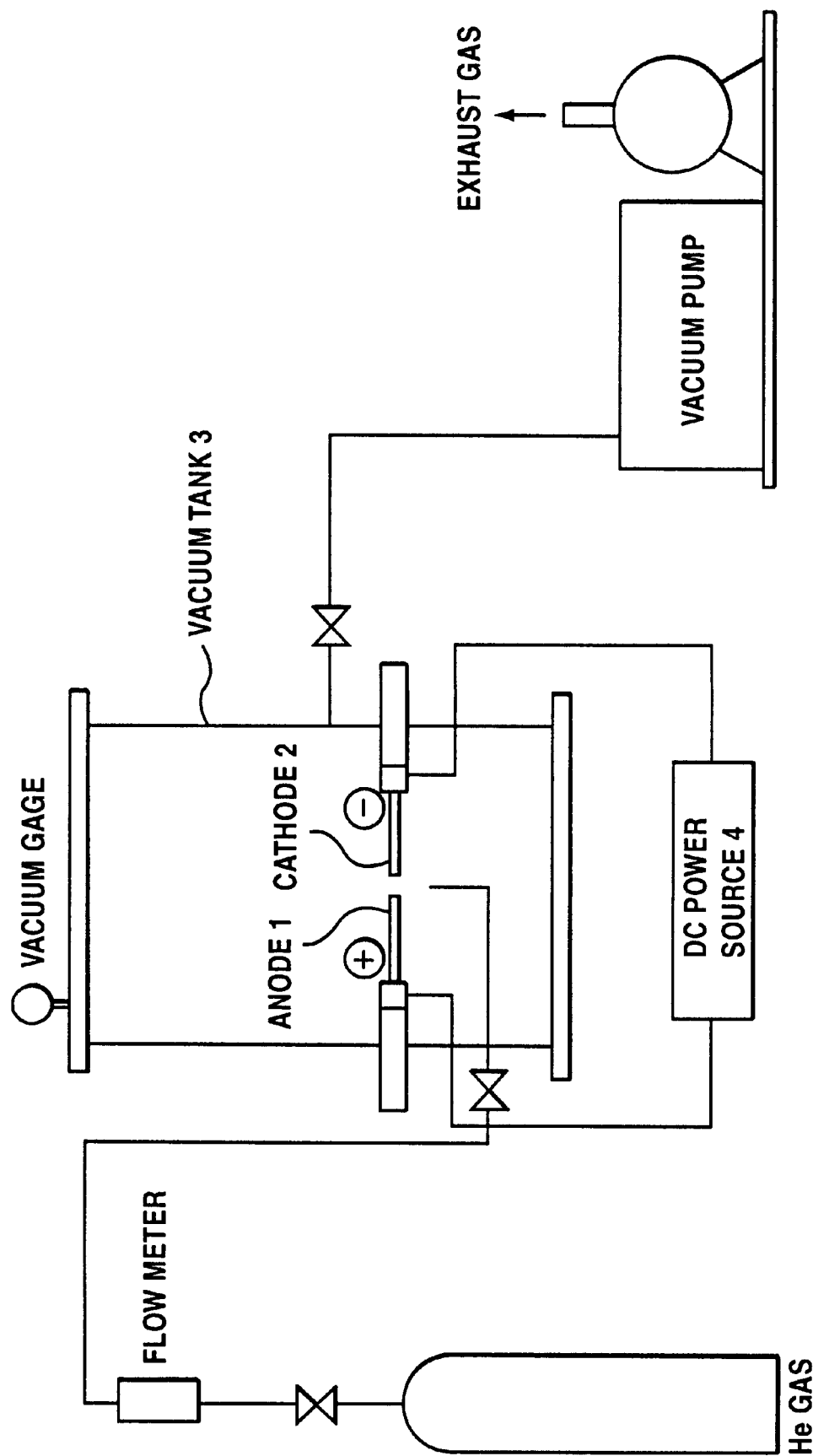
FIG. 1 is a perspective view illustrating an arc discharge apparatus used in EXAMPLE 1.

The carbon mixture as a gas sensor material of the present invention is obtained by arc discharge using carbon electrodes in an inert gas.

Conventional vacuum devices for arc discharge may be used as an apparatus for producing the carbon mixture.

As inert gases, for example, helium, argon, neon, krypton, xenon, and the like may be used. The pressure of the inert gas may be about 0.1 to 600 torr, preferably about 10 to 400 torr.

As electrodes for the arc discharge in producing the carbon mixture, carbon electrodes are used for both a cathode and an anode.

The arc discharge may be conducted by passing an alternating current or a direct current, wherein the electric current density on the discharge surfaces of the carbon electrodes, or the electric current density on opposite surfaces of a cathode and an anode facing each other and spaced at a specified distance is about 0.8 to 3.5 $A/mm^2$.

The carbon mixtures obtained by such a method may be used for the gas sensor materials of the present invention. The carbon mixture is so-called carbon soot, which can be obtained as powder attached to the inside of the apparatus. The carbon mixture comprises ultrafine carbon grains having a size of about φ1 nm to 100 μm, which are mainly composed of graphite carbon, indeterminately-formed carbon, and fullerenes, wherein the fullerenes are contained at about 0.1 to 15% by weight.

In the present invention, such gas sensor materials that contain metal components in the above carbon mixture may also be used. The sensing ability can be improved by adding such a metal component into the carbon mixture. Further, the gas sensor shows a peculiar property in accordance with the metal species contained therein and is improved in selectivity against gases. For example, in the case of using a nickel-containing carbon mixture, output form in direct current becomes very peculiar under an atmosphere of nitrogen trifluoride, so that the identification of the gas species becomes easier.

As the metal components of the metal-containing carbon mixture for the subject sensor materials, metals of a typical element and transition metals may be used. For example, B, Mg, Al, Si, In, and the like may be listed as the metals of a typical element while La, Ni, Co, Fe, Cr, Ta, Mn, Mo, Ti, Au, Pd, Pt, Ag, and the like may be listed as the transition metals. These metal components may be used alone or in combination of two or more, wherein a suitable content is about 0.01 to 30% by weight.

The metal-containing carbon mixture can be obtained by arc discharge in an inert gas using the metal-containing carbon electrodes in the same manner as obtaining the carbon mixture. The shape and the like of the metal-containing carbon electrodes may not be specifically limited and may be the same as those electrodes conventionally used for arc discharge, while the metal content in the electrode may be arranged in such a manner that the metal content of the electrodes disappearing as evaporation by arc discharge may be the same as that of the carbon mixture produced by the arc discharge. As to methods to provide the electrode with metal, there are a method wherein carbon and metallic powder are homogeneously mixed so as to be formed into an electrode, a method wherein metal in a form of powder, line, block, or the like is filled into a cavity made in an electrode, or the like, either which will do. The conditions for the arc discharge to produce a metal containing mixture may be the same as those for the carbon mixture above.

The resultant matter obtained by the arc discharge using the metal-containing carbon electrodes is a mixture of ultrafine carbon grains having a size of the order of 1 nm to 100 $\mu$m and metallic ultrafine grains having the same size as the above carbon mixture. The ultrafine carbon grains are composed of graphite carbon, indeterminately-formed carbon, and fullerenes, wherein the fullerenes are generally contained at about 0.1 to 15% by weight in the ultrafine carbon grains. The metal content in the metal-containing carbon mixture is the same as that of the electrode, which disappears as evaporation by the arc discharge.

According to the present invention, a gas sensor can be obtained by using the carbon mixture or the metal-containing carbon mixture as a sensor material obtained by the above methods. The shape of the gas sensor may not be specifically limited and may be the same as that of various conventional gas sensors. For example, the carbon mixture or the metal-containing carbon mixture may be formed into a pellet or a sphere or the like, the carbon mixture or the metal-containing carbon mixture may be formed into paste so as to be printed on a ceramic substrate, or metal of MOS transistor may be replaced with the carbon mixture or the metal-containing carbon mixture so as to be formed into a FET type. The methods for forming a compact may not be specifically limited. For example, the carbon mixture or the metal-containing carbon mixture may be pressed at high pressure. Alternatively, the carbon mixture or the metal-containing carbon mixture may be mixed with a binder such as hydrocarbons (e.g., paraffin), polyvinyl acetate plastics, polyvinyl alcohol, carboxymethyl cellulose, oil pitch, coal pitch, which are contained at the order of 5 to 10% by weight based on the whole amount, dispersed in media such as water, alcohols, methyl cellosolve, or the like. This mixture then may be formed into a desired shape, solidified and dried, and heated at about 200° C. to 300° C., and then may be baked at about 400° C. to 900° C., if necessary, thereby resulting in a compact. Alternatively, colloidal silica may be added at about 1 to 20% by weight into the carbon mixture or the metal-containing carbon mixture, and then formed and dried at a temperature from room temperature to 200° C. A metal alkoxide solution (e.g., a solution containing 25 g of $Si(OC_2H_5)_4$, 37.6 g of $C_2H_5OH$, 23.5 g of $H_2O$, and 0.3 g of HCl) may be added at about 1 to 30% by weight in the carbon mixture or the metal-containing carbon mixture and dried at a temperature from room temperature to about 200° C. so as to form a compact.

Since output voltage or current varies in accordance with gas concentration in these gas sensors, it is possible to detect the gas. In addition, it is possible to detect the change in frequency of a hydrogen oscillator with a change in weight by fixing the carbon mixture or the metal-containing carbon mixture to the hydrogen oscillator so as to adsorb the gas.

According to a gas sensor using the sensor materials of the present invention, it is possible to detect a gas at a room temperature. However, since the sensitivity may be inferior according to the gas species, the sensor may be heated to about 50° C. to 200° C. to improve the sensitivity. As a method of heating, a gas may continuously be heated to a fixed temperature. Alternatively, since the sensor material of the present invention has properties that it adsorbs a gas at ordinary temperatures while it emits the adsorbed gas when heated, a gas can be detected as compulsorily exhausting the adsorbed gas with pulse heating.

The gas sensor materials of the present invention have peculiar properties that they respond to a polar gas, while they scarcely respond to a nonpolar gas such as methane, butane, and isobutane. Since the output form of current or voltage differs according to the kind of polar gas, it is easy to identify the gas species by using this property. Namely, the sensor materials are superior in selectivity. As examples of polar gases which can be detected by using the sensor materials of the present invention, ammonia or a gas containing an amino group, amines such as methyl amine, sulfur compounds such as methyl mercaptan, or a gas containing a thiol group, oxides such as NOx and Sox, or a gas containing oxygen atoms, CFs such as methane trifluoride bromide and dichloromethane difluoride, or nitrogen trifluoride ($NF_3$), or a gas containing fluorine atoms, chlorinated compounds such as dichlorosilane, trichlorosilane, or the like, or a gas containing chlorine atoms, hydrogenated compounds, such as arsine ($AsH_3$), phosphine ($PH_3$), or a gas containing hydrogen atoms, or the like, may be listed.

EMBODIMENT

The present invention will now be further described with reference to the Examples.

EXAMPLE 1

A carbon mixture was produced by using an arc discharge apparatus having carbon electrodes as shown in FIG. 1. In the apparatus, carbon electrodes having $\phi$20 mm and 500 mm length were used as anode 1 and cathode 2. After evacuating the inside of a vacuum tank 3, helium gas was introduced into the vacuum tank 3 so that the pressure was 100 torr. Then, a direct current was passed to carbon electrodes 1 and 2 by using a DC power source 4 for arc discharge so that the current density on the discharge faces (opposite faces on each of the electrodes) become about 2 $A/mm^2$, and the carbon mixture was evaporated. Thereafter, a nitrogen gas for industrial use was introduced into the vacuum tank 3, so that the pressure was at atmospheric pressure and the carbon mixture attached to the inside of the vacuum tank 3 was taken out.

0.2 g of the thus obtained carbon mixture was put into a die of φ14 mm, was loaded with load of 1 ton by a presser, and was formed into a pellet.

A test for detecting an ammonia gas by using the thus obtained pellet at a room temperature by the following four-terminal method then was conducted.

Figure 2:
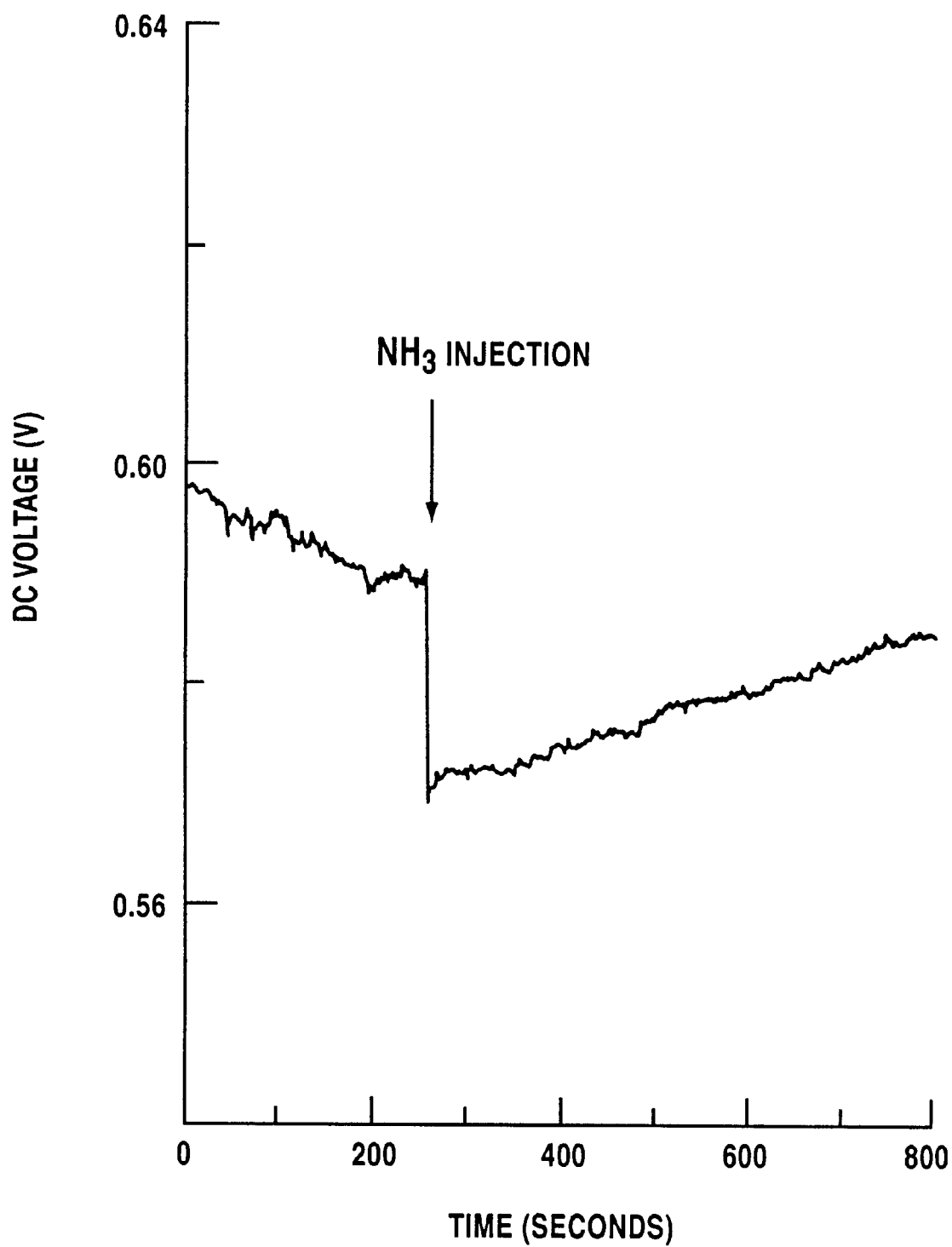
FIG. 2 is a graph showing test results for sensing an ammonia gas using the carbon mixture obtained in EXAMPLE 1.

An acrylic container with a gas stirring fan having a capacity of 5,400 ml was prepared. The above pellet made of the carbon mixture was placed on the inside bottom of the acrylic container. Four terminals are aligned in line with 2 mm intervals on the surface of the pellet and 0.09 mA DC was passed to the two end terminals. The output voltage was measured on the internal two terminals. After the output became steady, 5 ppm of ammonia was injected into the container by a micro syringe, a time-course change of the output current was obtained and its results are shown in FIG. 2. From these results, it is found that the above carbon mixture shows good responsiveness to an ammonia gas at room temperature.

EXAMPLE 2

A cylindrical hole of φ3.2 mm with 15 mm depth was made on a central part of a bottom of a cylindrical carbon electrode of φ20 mm and 500 mm length and the hole filled wits. 0.9 g of nickel powder (of 200 mesh) so that nickel-containing electrodes were produced. Thus obtained electrodes were used as anode 1 and cathode 2. The surfaces on which nickel was filled were placed so as to face each other at a fixed interval for electric discharge. Using the same arc discharge apparatus having carbon electrodes as in EXAMPLE 1, arc discharge was conducted at the same conditions as those of EXAMPLE 1, so that the electrodes were evaporated. As result, a nickel-containing carbon mixture was obtained as deposited on the inside of the vacuum tank. The thus obtained carbon mixture contained 2.95% by weight of nickel with a particle size of about 200 Å.

By using the thus obtained nickel-containing carbon mixture as a gas sensor material, a test for detecting a gas was conducted.

Figure 3:
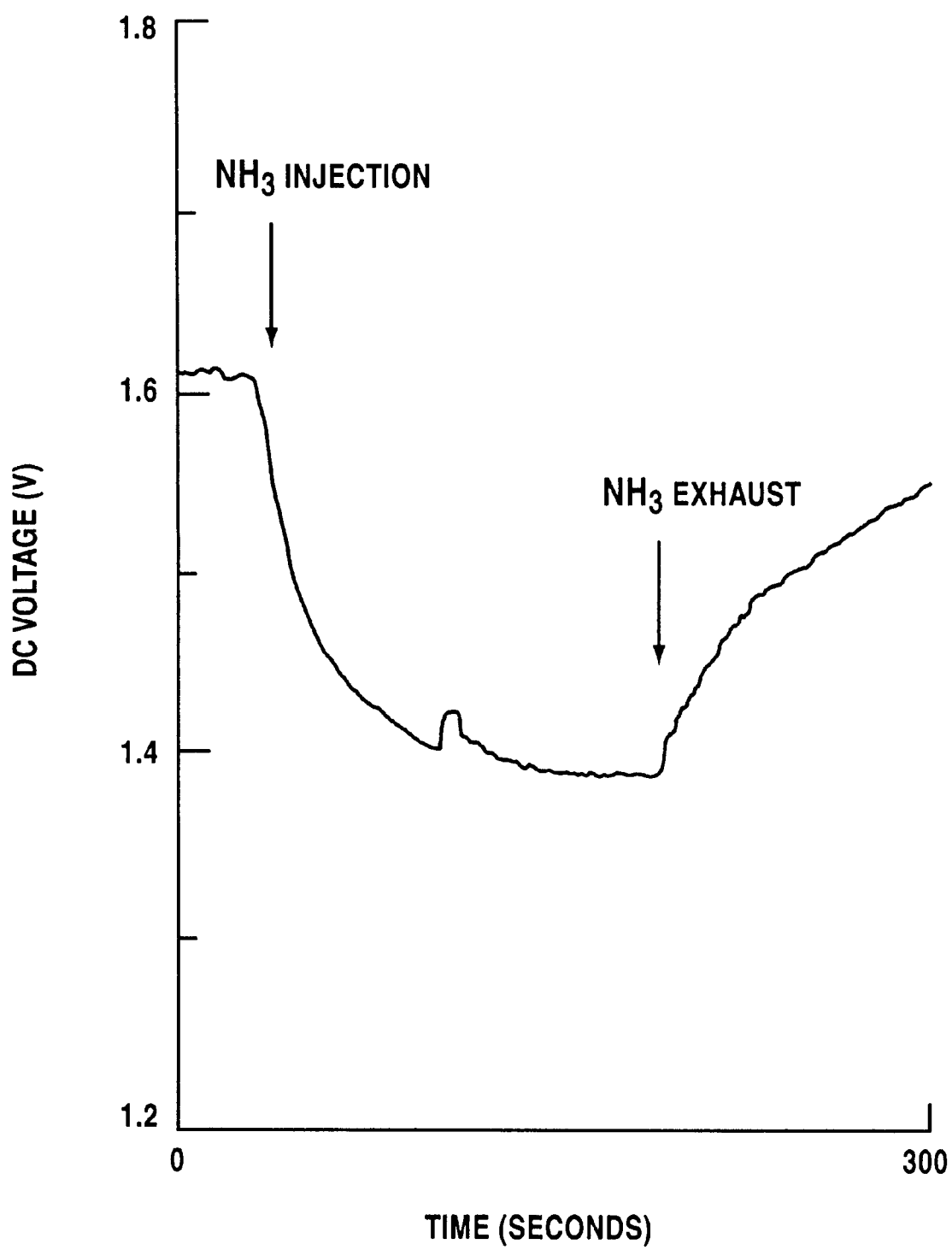
FIG. 3 is a graph showing test results for sensing an ammonia gas using the Ni-containing carbon mixture obtained in EXAMPLE 2.

The same apparatus as that of EXAMPLE 1 was used and the nickel-containing carbon mixture was formed into a pellet. Four terminals were provided in the same way as EXAMPLE 1 and 0.1 mA current was passed to the two end terminals. After 5 ppm of an ammonia gas was injected into the container by a micro syringe, a change in DC output was obtained when the lid of the container was opened after a specific time has passed. The results are shown in FIG. 3.

Figure 4:
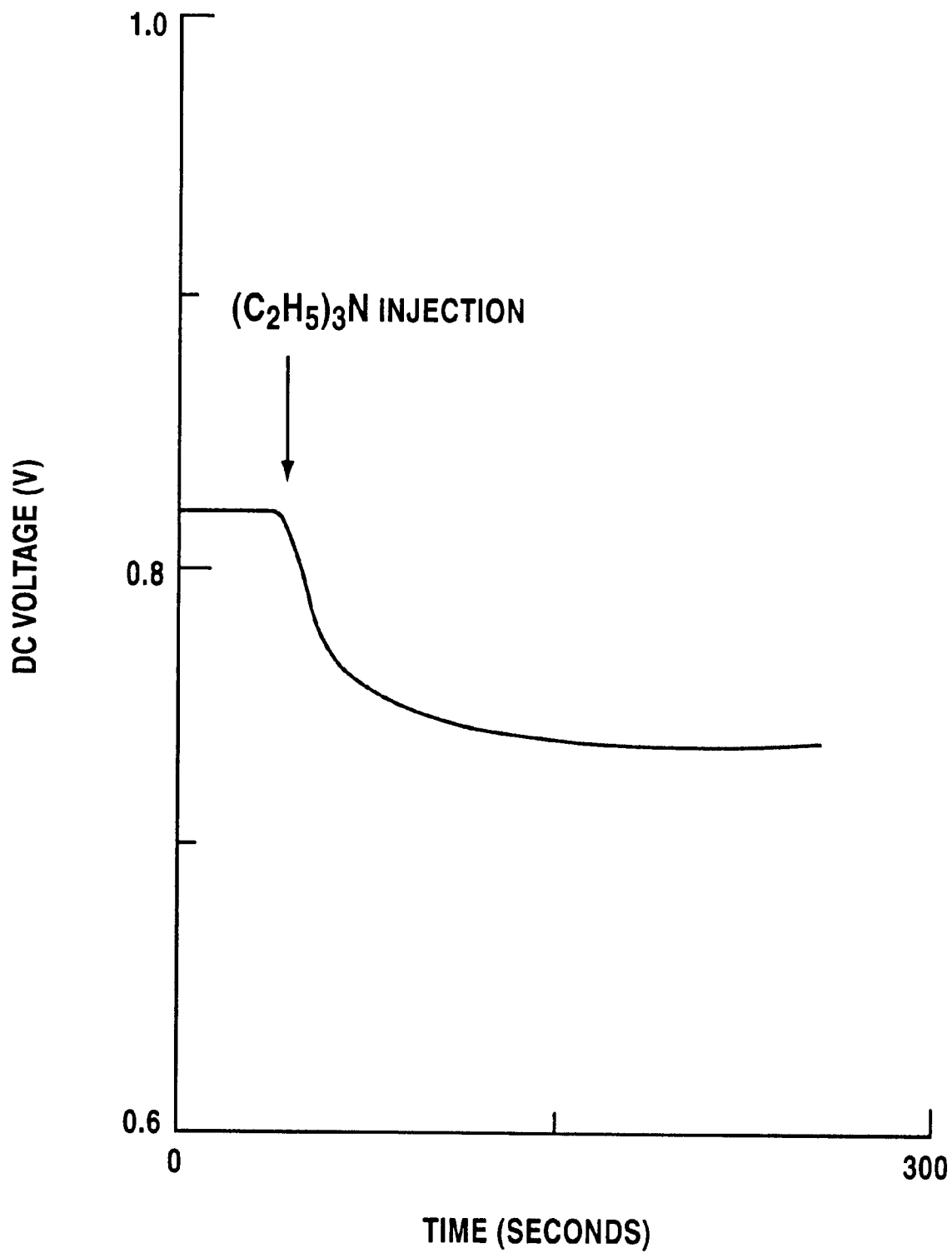
FIG. 4 is a graph showing test results for sensing triethylamine using the Ni-containing carbon mixture obtained in EXAMPLE 2.

Four terminals were provided in the same way as EXAMPLE 1 and 0.1 mA current was passed to the two end terminals. After 10 μl of triethylamine was injected into the container by a micro syringe, a change in DC output was obtained. The results are shown in FIG. 4.

Figure 5:
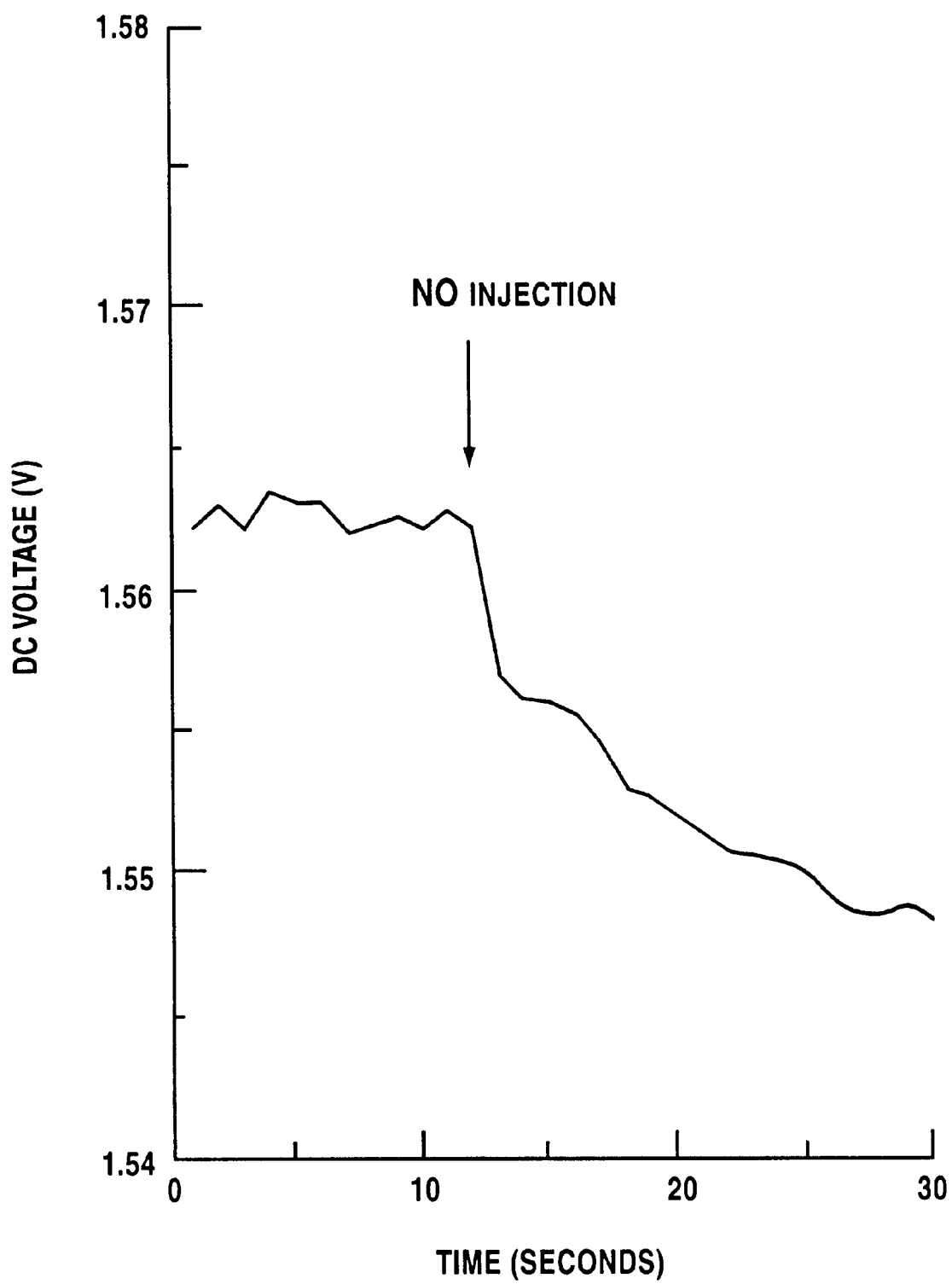
FIG. 5 is a graph showing test results for sensing a nitrogen monoxide gas using the Ni-containing carbon mixture obtained in EXAMPLE 2.
Figure 6:
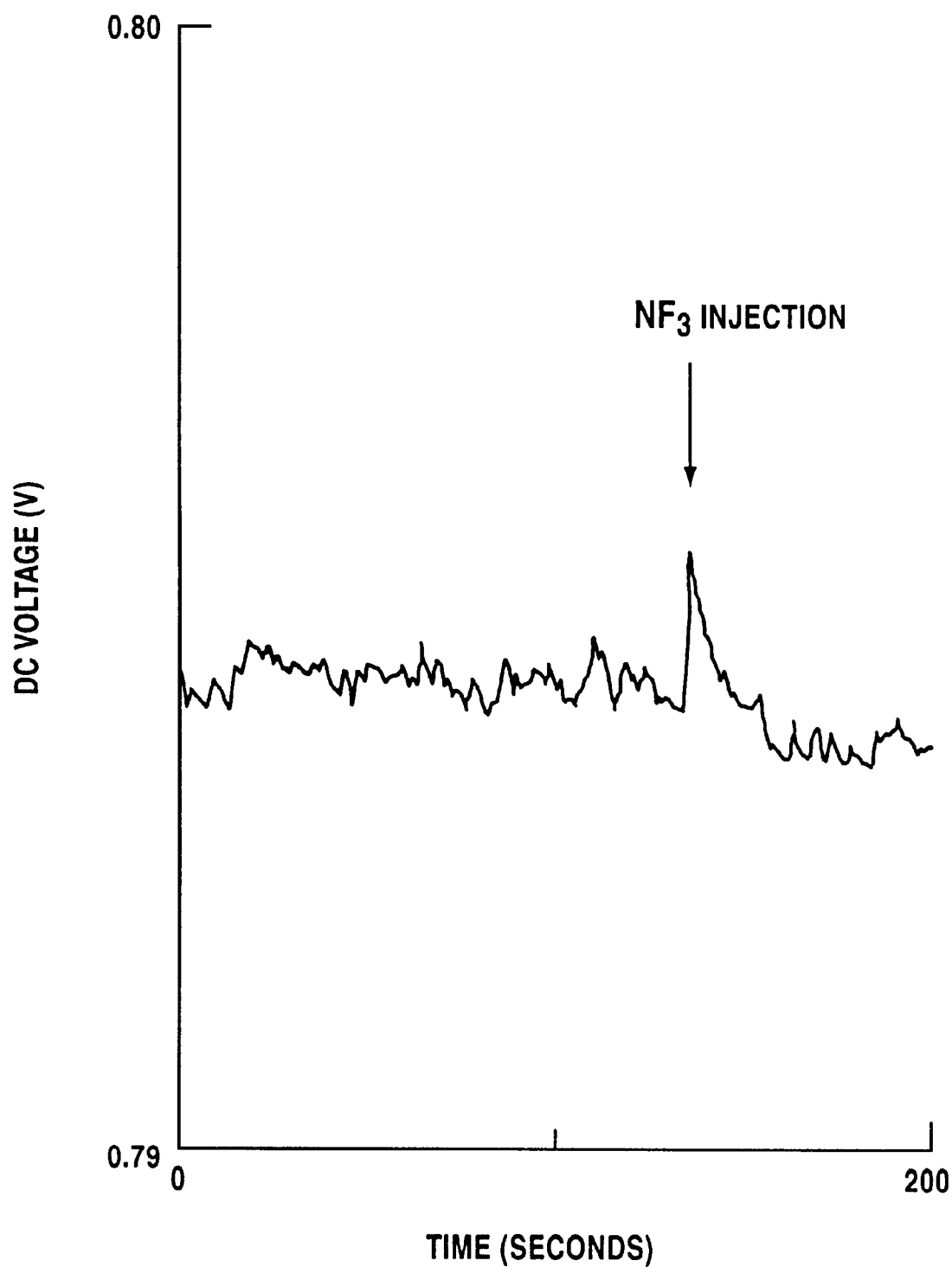
FIG. 6 is a graph showing test results for sensing a nitrogen trifluoride gas using the Ni-containing carbon mixture obtained in EXAMPLE 2.

Further, four terminals were provided on the pellet made of nickel-containing carbon mixture by using the same test apparatus and 0.1 mA current was passed to the two end terminals. After 8 ppm of a nitrogen monoxide gas or a nitrogen trifluoride gas was injected into the container by a micro syringe, a change in DC output was obtained. The results for a nitrogen monoxide gas are shown in FIG. 5 while those for a nitrogen trifluoride gas are in FIG. 6.

As apparent from the above results, the nickel-containing carbon mixture shows superiority in sensitivity to various polar gases and also selectivity of gas species because it shows each peculiar output form in accordance with the difference of gas species. Particularly, it is easy to identify an nitrogen trifluoride gas, since the output current form of the gas is special and different from other gases.

INDUSTRIAL APPLICABILITY

The gas sensor material of the present invention uses the carbon mixture or metal-containing carbon mixture obtained by arc discharge as it is, that is, without purification. Therefore, since no purification and the like is necessary, there is no trouble in generating wastes accompanying to a purification and any cost increase.

Further, since the gas sensor materials enable gas detection at room temperature and shows superiority in gas selectivity, the materials are very useful.

What is claimed is:

1. A gas sensor comprising a main body formed of carbon mixture and terminals provided on the main body at a predetermined interval for measuring an output voltage or an output current between terminals, the carbon mixture having been obtained as evaporated matter by arc discharge generated by passing an alternating current or a direct current with electric current density of 0.8 to 3.5 A/mm$^2$ on discharge surfaces of carbon electrodes in an inert gas under a pressure of 0.1 to 600 torr.

2. A gas sensor comprising a main body formed of metal-containing carbon mixture and terminals provided on the main body at a predetermined interval for measuring an output voltage or an output current between the terminals the metal-containing carbon mixture have been obtained as evaporated matter by arc discharge generated by passing an alternating current or a direct current with electric current density of 0.8 to 3.5 A/mm$^2$ on discharge surfaces of carbon electrodes containing 0.01 to 30% by weight of metal in an inert gas under a pressure of 0.1 to 600 torr.

* * * * *